United States Patent
Song et al.

(10) Patent No.: US 12,405,259 B2
(45) Date of Patent: Sep. 2, 2025

(54) RAPID UAV-BASED MONITORING AND DISCRIMINATION METHOD FOR DROUGHT IN SUMMER MAIZE BASED ON CHLOROPHYLL CONTENT

(71) Applicant: China Institute of Water Resources and Hydropower Research, Beijing (CN)

(72) Inventors: Wenlong Song, Beijing (CN); Mengyi Li, Beijing (CN); Changjun Liu, Beijing (CN); Pu Zhou, Beijing (CN); Lang Yu, Beijing (CN); Yizhu Lu, Beijing (CN); Yun Liu, Beijing (CN); Wenjing Lu, Beijing (CN); Xiuhua Chen, Beijing (CN); Long Chen, Beijing (CN)

(73) Assignee: China Institute of Water Resources and Hydropower Research, Beijing (CN)

( * ) Notice: Subject to any disclaimer, the term of this patent is extended or adjusted under 35 U.S.C. 154(b) by 0 days.

(21) Appl. No.: 18/991,999

(22) Filed: Dec. 23, 2024

(65) Prior Publication Data
US 2025/0130216 A1    Apr. 24, 2025

Related U.S. Application Data

(63) Continuation of application No. PCT/CN2023/119395, filed on Sep. 18, 2023.

(30) Foreign Application Priority Data

Sep. 20, 2022 (CN) .......................... 202211140492.5

(51) Int. Cl.
G06Q 10/04    (2023.01)
G01N 33/00    (2006.01)
(Continued)

(52) U.S. Cl.
CPC ......... *G01N 33/0098* (2013.01); *G06V 20/17* (2022.01); *G06V 20/188* (2022.01); *G06V 20/194* (2022.01)

(58) Field of Classification Search
CPC .. G01N 33/0098; G01N 33/025; G01N 21/27; G01N 21/251; G01N 2021/1797;
(Continued)

(56) References Cited

U.S. PATENT DOCUMENTS 12,141,730 B2 * 11/2024 Singh .................... G06V 20/188
2019/0339242 A1 * 11/2019 Wang ..................... G01N 21/31
2023/0384231 A1 * 11/2023 He ...................... G01N 33/0098

FOREIGN PATENT DOCUMENTS

| CN | 106355143 A | 1/2017 |
| CN | 106780079 A | 5/2017 |

(Continued)

OTHER PUBLICATIONS

Internation Search Report of PCT/CN2023/119395, Mailed Jan. 5, 2024.
(Continued)

*Primary Examiner* — Jeffrey P Aiello (57) ABSTRACT

A rapid monitoring and discrimination method for drought conditions in summer maize based on chlorophyll content includes: 1) Obtaining multi-spectral imagery through UAV multi-payload low-altitude remote sensing technology and measuring chlorophyll content on the ground. Additionally, calculating vegetation indices including Normalized Difference Vegetation Index (NDVI), Soil-Adjusted Vegetation Index (SAVI), and Renormalized Difference Vegetation Index (RENDVI). 2) Selecting vegetation indices and constructing regression equations with measured chlorophyll content during different growth stages. The regression equation with the highest correlation for each growth stage is chosen as the optimal model equation for that particular (Continued)

stage. 3) Using the optimal model equations to retrieve chlorophyll content for each period and determining thresholds for chlorophyll content across different drought levels through calibration. 4) Calculating the required vegetation indices from real-time multi-spectral imagery of the field under test, retrieving chlorophyll content, and comparing it with the established thresholds to assess the real-time drought level.

4 Claims, 10 Drawing Sheets

(51) Int. Cl.
*G06Q 50/02* (2024.01)
*G06T 7/00* (2017.01)
*G06T 7/90* (2017.01)
*G06V 20/10* (2022.01)
*G06V 20/17* (2022.01)

(58) Field of Classification Search
CPC ......... G01N 2021/8466; G06V 20/188; G06V 20/194; G06V 20/17; G06V 10/82; G06V 10/58; A01B 79/005; A01B 79/02; A01G 7/00; G06Q 50/02; G06Q 10/063; G06Q 10/0639; G06T 2207/30188; G06T 2207/10036; G06T 2207/20081; G06T 2207/10024; G06T 2207/10048; B64C 39/02; B64C 39/024; G06F 17/12; G06F 17/13; G06F 17/11; G06F 30/27

USPC ........ 702/188, 86, 127, 128, 104; 703/11, 2, 703/12; 800/320.1

See application file for complete search history.

(56) References Cited

FOREIGN PATENT DOCUMENTS

| | | | |
|---|---|---|---|
| CN | 107024439 A | 8/2017 | |
| CN | 108629494 A | 10/2018 | |
| CN | 108760660 A | 11/2018 | |
| CN | 109115725 A | 1/2019 | |
| CN | 110567891 A | 12/2019 | |
| CN | 111028096 A * | 4/2020 | |
| CN | 111965117 A | 11/2020 | |
| CN | 112231638 A | 1/2021 | |
| CN | 113008843 A | 6/2021 | |
| CN | 113268923 A | 8/2021 | |
| CN | 110647786 B * | 4/2022 | ......... G06K 9/00657 |
| CN | 115950838 A | 4/2023 | |
| WO | 2022175236 A1 | 8/2022 | |

OTHER PUBLICATIONS

Liu Tao et al., "Estimation of the Leaf Area Index and Chlorophyll Content of Wheat Using UAV Multispectrum Images", Transactions ofthe Chinese Society, of Agricultur, Engineering, vol. 37, No. 19, Oct. 31, 2021, pp. 66-69, sections 1-2.
Wei Qing et al., "Estimation of Canopy Chlorophyll Content in Winter Wheat by UAV Multispectral Remote Sensing", Journal of Triticeae Crops, vol. 40, No. 3, Jan. 7, 2020, pp. 367-370.

* cited by examiner

RAPID UAV-BASED MONITORING AND DISCRIMINATION METHOD FOR DROUGHT IN SUMMER MAIZE BASED ON CHLOROPHYLL CONTENT

TECHNICAL FIELD

The invention pertains to the field of drought monitoring, particularly to the monitoring of drought in summer maize, and specifically to a rapid UAV-based monitoring and discrimination method for drought in summer maize based on chlorophyll content.

BACKGROUND

Drought is a major natural factor affecting crop growth and yield, and prolonged and widespread drought can result in significant crop yield reductions. Precipitation and irrigation are the primary sources of water during crop growth and development. Maize is a water-loving crop and is sensitive to water stress. Water deficiency can inhibit normal physiological metabolic activities in maize, affect its normal growth and development, and reduce yield by 20% to 30% in average years, and even lead to widespread crop failures in severe years. Agricultural infrastructure in China is weak, and irrigation techniques and systems are not well-developed. Currently, most regions still use traditional methods of flood irrigation, which results in uneven irrigation and inefficient water use. Maize has different water requirements at different stages. From emergence to the jointing stage, maize plants are small, grow slowly, and have low water demand, with soil moisture controlled at around 60% of field capacity. From the tasseling stage to the milk-ripe stage, maize plants grow rapidly and are very sensitive to water. Water demand peaks during the tasseling and flowering stages, and water shortage will have severe impacts, reducing yield by 20%-50%. During the maturity stage, water demand is only 4%-7%. Therefore, timely irrigation is necessary to ensure normal growth of maize plants according to their different water demands. Soil moisture conditions during maize growth and development can reflect vegetation moisture conditions. If soil moisture is insufficient, the physiological water needs of crops cannot be met, severely affecting normal crop growth and development and productivity. These inhibitory effects manifest in physiological parameters and appearance, but changes in these parameters are complex. Manually observing these parameters is time-consuming, labor-intensive, poor in spatial representation, and can damage plants, making it difficult to conduct long-term, effective, and high-precision observations of vegetation.

Currently, maize drought monitoring is mainly implemented through soil moisture monitoring and assessment and vegetation index-based remote sensing monitoring. However, the physical mechanisms are not well-defined, and it is time-consuming and labor-intensive, resulting in low accuracy and efficiency of large-scale drought monitoring.

Remote sensing technology can better reflect changes in soil moisture and can quickly, efficiently, and non-destructively obtain drought information. However, remote sensing imagery is affected by factors such as resolution, weather, and revisit cycles, which can easily lead to data loss, temporal discontinuity, and low spatial resolution. There are two main types of vegetation drought remote sensing monitoring methods: one is based on water content, and the other is the remotely sensed drought index method, which is most widely used in current practical drought monitoring systems. Indices can better reflect changes in soil moisture, but due to the lack of mechanistic understanding in agricultural drought remote sensing monitoring and the scarcity of agricultural drought remote sensing monitoring indicators, the in-depth application of crop drought remote sensing monitoring is limited.

UAV-based crop monitoring has become a research focus. UAVs can obtain high-precision remote sensing data at any time and can leverage their advantages in fine-scale and dynamic continuous monitoring of farmland. UAV-based low-altitude remote sensing technology can provide rapid and convenient services for information monitoring in large field areas.

UAV-based low-altitude remote sensing monitoring has unique technical advantages such as regional monitoring, high spatio-temporal resolution, operation under clouds, flexibility, low cost, rapidness, and efficiency. It can achieve fine-scale and dynamic continuous monitoring of farmland and has been widely applied to drought monitoring. However, existing UAV drought monitoring mainly focuses on onions and fruit trees, with relatively little monitoring of field crops, which cannot meet the needs of precision irrigation in agriculture.

Chlorophyll is an important pigment involved in photosynthesis within chloroplasts and is an important parameter for evaluating the healthy growth status of crops. The most intuitive manifestation of crops under drought stress is leaf yellowing. Therefore, estimating the chlorophyll content of green vegetation is of great significance for the healthy growth of crops. Currently, UAV low-altitude remote sensing is used for summer maize monitoring, but there is little research on delineating chlorophyll content thresholds for different drought levels, and this technology is not yet mature.

SUMMARY OF THE INVENTION

The purpose of the invention is to propose a method for rapidly monitoring and discriminating drought in summer maize based on chlorophyll content analysis, to improve detection accuracy and monitoring efficiency under different drought conditions, based on the aforementioned technical deficiencies.

The purpose of the invention is achieved as follows:

A rapid UAV-based monitoring and discrimination method for drought conditions in summer corn, which relies on chlorophyll content, includes the following steps:

1) Data Acquisition: This involves collecting multispectral imagery data using unmanned aerial vehicle (UAV) multi-payload low-altitude remote sensing technology, along with ground-measured leaf area index (LAI) data. From the multispectral imagery data, NDVI, SAVI, and RENDVI vegetation indices are calculated.

2) Construction of Chlorophyll Content Inversion Models for Different Drought Levels During Various Growth Stages of Summer Maize: The NDVI-OTSU method is employed to eliminate soil background and extract pure vegetation index pixel values for the summer maize canopy. NDVI, RENDVI, and SAVI vegetation indices are selected to construct three types of regression equations with measured chlorophyll content across different growth stages, namely, jointing, heading, silking, and maturity. The regression equation with the highest correlation to chlorophyll content for each growth stage is chosen as the optimal model equation for that stage. The three types of regression equations include linear, exponential, and logarithmic equations.

3) Calibration of Chlorophyll Content Thresholds for Different Drought Levels: Based on the optimal model equations obtained in Step 2) for each growth stage, chlorophyll content is inverted for each stage, and thresholds for chlorophyll content across different drought levels are calibrated.

4) Real-time Discrimination of Drought Severity Levels: Multispectral imagery of the plot to be tested is obtained through real-time monitoring, and the required vegetation index is calculated. This vegetation index is then input into the optimal model equation for the corresponding growth stage calibrated in Step 2) to invert the chlorophyll content value. This chlorophyll content value is then compared with the thresholds for that period obtained in Step 3) to determine the real-time drought severity level.

Further Optimization: For the acquisition of multispectral imagery data mentioned in Step 1), an FL-81 quadrotor UAV integrated with a MicaSense RedEdge-M™ multispectral camera is used to capture multispectral aerial images. The flight altitude is set at 55 m, corresponding to a ground resolution of 4 cm. The camera's lens captures wavelengths in the blue, green, red, red-edge, and near-infrared bands.

For the measured chlorophyll content mentioned in Step 1), the chlorophyll content analyzer SPAD-502Plus is used to measure SPAD values. Eight plants per plot are selected to measure the relative chlorophyll content (SPAD) of their leaves, with the average value serving as the SPAD value for that plot. The formula for calculating the absolute chlorophyll content $Cab/\mu g \cdot cm^{-2}$ of the leaves is as follows:

$$Cab = 0.11 SPAD^{1.5925}.$$

Further, in Step 2), the optimal model equations for different growth stages are as follows: for the jointing stage, it is a logarithmic regression model between SAVI and chlorophyll content; for the heading stage, it is a linear regression model between RENDVI and chlorophyll content; for the silking stage, it is a logarithmic regression model between NDVI and chlorophyll content; and for the maturity stage, it is an exponential regression model between RENDVI and chlorophyll content.

Further, in Step 3), the calibrated chlorophyll content thresholds for different drought levels are as follows: for the jointing stage, normal conditions are above 54.9, mild drought is between 53.1 and 54.9, moderate drought is between 51.0 and 53.1, and severe drought is below 51.0; for the heading stage, normal conditions are above 65.4, mild drought is between 59.2 and 65.4, moderate drought is between 54.1 and 59.2, and severe drought is below 54.1; for the silking stage's leaf area index (LAI), normal conditions are above 60.0, mild drought is between 56.1 and 60.0, moderate drought is between 52.0 and 56.1, and severe drought is below 52.0; for the maturity stage's LAI, normal conditions are above 55.5, mild drought is between 47.8 and 55.5, moderate drought is between 43.5 and 47.8, and severe drought is below 43.5.

Further, the calibration method for chlorophyll content thresholds between different drought levels in Step 3) is as follows: First, calculate the average inversion results for plots with different drought levels. Then, calculate the median of the averages for adjacent drought level plots and use it as the threshold between the two adjacent drought levels.

Taking the calibration of thresholds for the jointing stage as an example, calculate the vegetation indices of NDVI, SAVI, and RENDVI, perform regression analysis between each vegetation index and measured chlorophyll content to construct models based on linear, exponential, and logarithmic relationships, and determine that the regression model with the highest correlation for the jointing stage is the logarithmic model between SAVI and chlorophyll content. Invert SAVI to obtain chlorophyll content results for summer maize under different drought levels, thereby classifying thresholds for normal, mild drought, moderate drought, and severe drought and determining the threshold ranges. First, calculate the averages for each drought level, then calculate the median between the normal average and the mild drought average, and use this median as the threshold to distinguish between the two drought levels. The same applies to mild drought and moderate drought, and moderate drought and severe drought.

The advantages and beneficial effects of this invention are:

The method of this invention for monitoring and discriminating drought conditions in summer maize has high accuracy. The extraction of thresholds is flexible, stable, and rapid. By comparing and analyzing, the best chlorophyll content inversion model for each growth stage is obtained, and thresholds for chlorophyll content at different drought levels are calibrated to achieve rapid and high-precision drought monitoring and discrimination. This method can be used to quickly and efficiently assess drought conditions in large areas of summer maize, with convenient operation and high accuracy.

BRIEF DESCRIPTION OF THE DRAWINGS

The following further describes the invention in conjunction with the accompanying figures and embodiments.

DETAILED DESCRIPTION OF THE INVENTION

Embodiment 1

A Rapid UAV-Based Monitoring and Discrimination Method for Drought Conditions in Summer Corn Based on Chlorophyll Content Selection of Study Area and Preliminary Preparations:

The study area for this embodiment is located in the Donglei Phase II Yellow River Pumping Irrigation District of Fuping County, Weinan City, Shaanxi Province (109°10'–110°10'E, 34°41'-35°00'N). It is situated in the eastern part of the Guanzhong region of Shaanxi Province, to the west of the Yellow River and north of the Weihe River, within the northern part of the loess wavelike tableland area, with an altitude ranging from 385 m to 635 m. The irrigation district borders the Yellow River on the east, extends west to Fuping County Town, neighbors the "Shaanxi Jiaokou-Tiaowei Irrigation District" and "Weinan Luohui Canal Irrigation District" on the south, and is backed by the Qiaoshan Mountains on the north. The terrain is higher in the northwest and lower in the southeast. The climate is temperate continental monsoon, with cold and dry winters and hot and rainy summers. More than 50% of the rainfall occurs during summer, with an average annual rainfall of 519 mm-552 mm, which is significantly less than the average annual evaporation (1700 mm-2000 mm), making it a typical semi-arid region. The total area of the irrigation district is 1469.81 km2. The main crops in the irrigation district are wheat and corn.

Figure 1:
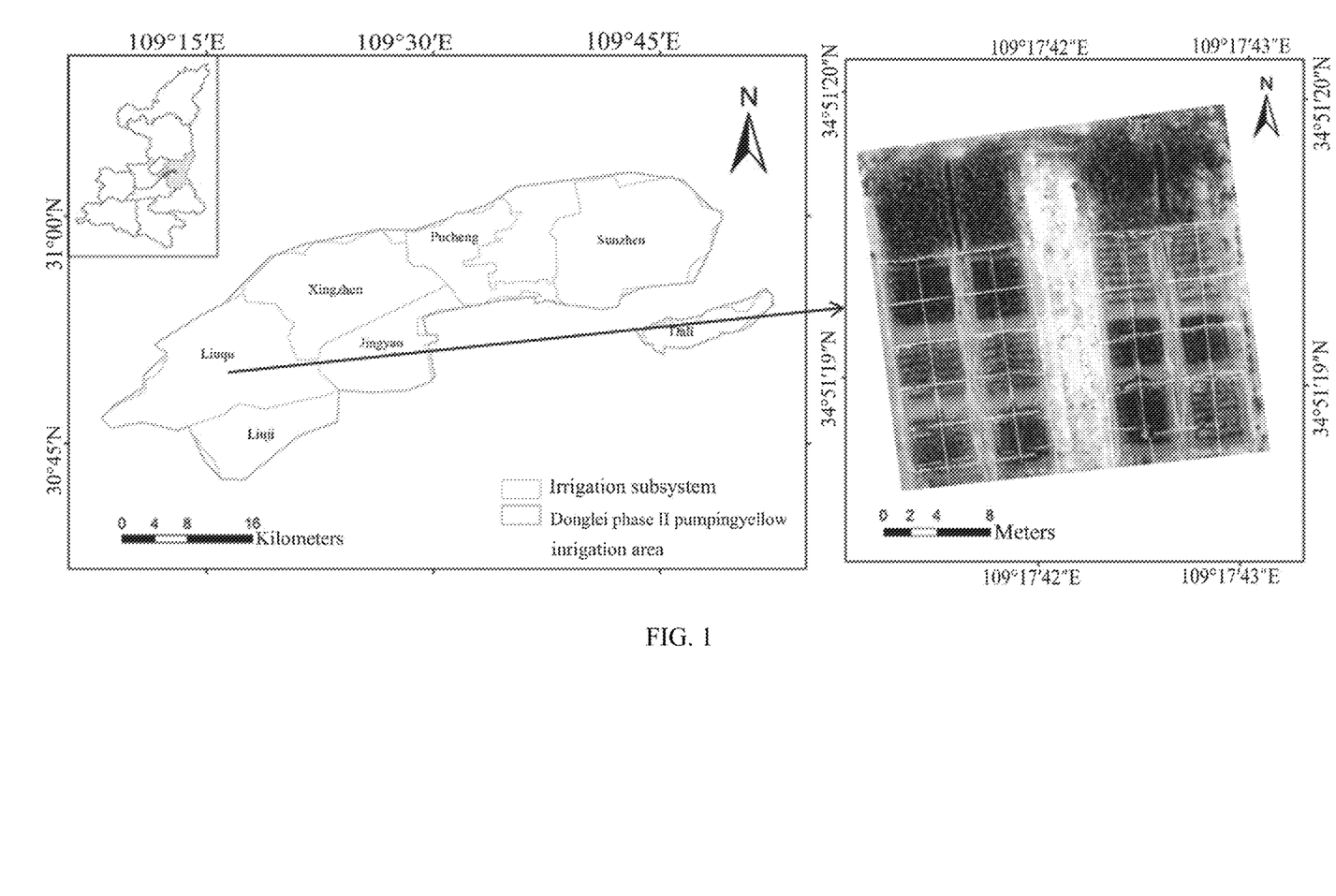
FIG. 1 shows an overview of the study area for Embodiment 1 of the invention.
Figure 2:
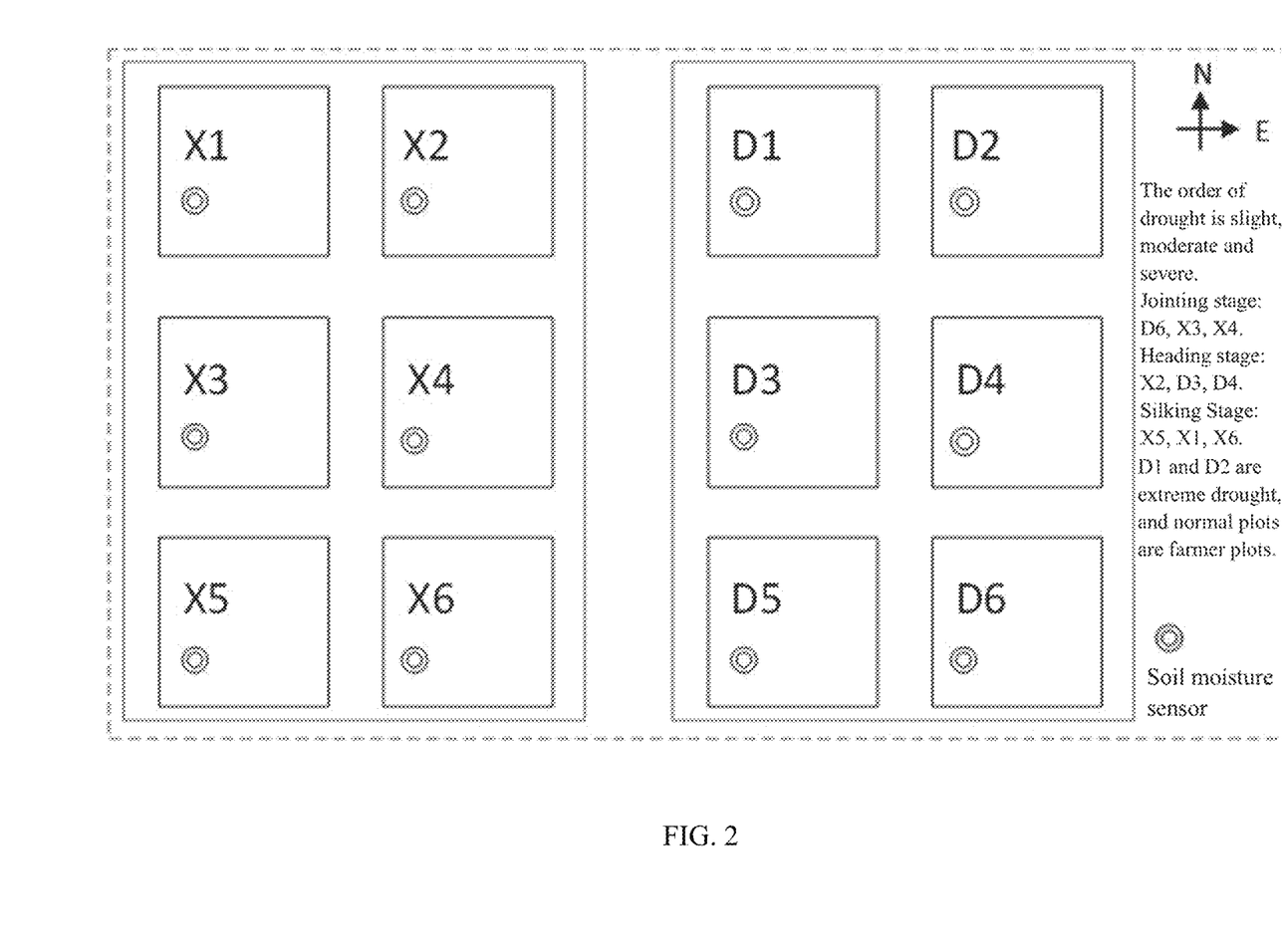
FIG. 2 shows the plot design for the study area in Embodiment 1 of the invention.

(1) Plot Design:

The experimental plots were selected on open and flat farmland with loamy soil, a groundwater depth of more than 2 m, and irrigation and drainage capabilities. Two plots, each with an area of 10 m 16 m, were set up. An openable and closable rain shelter was built above the plots to eliminate the impact of precipitation. The plots were evenly divided into 11 small 4 m4 m blocks. To ensure the implementation of water control experiments, a 2 m-wide isolation zone was maintained between the blocks to prevent seepage (FIG. 2). There were 17 soil moisture sensors installed in the experimental field, with 11 in one plot and 6 in another, providing observations with a time resolution of 30 minutes. The corn variety planted was Yufeng 620, a locally dominant variety, with row spacing of 70 cm and sowing depth of 3-5 cm. The sowing was done on June 27th, and conventional field management measures were followed during the growth process, referencing local farmer practices.

(2) Water Control Design:

The entire growth period of corn was divided into four stages, with detailed classifications as shown in Table 2-1. To ensure complete emergence, water treatments were initiated from the jointing stage until maturity, with five drought severity treatments designed (normal, mild drought, moderate drought, severe drought, and extreme drought). The classification of drought severity for corn was based on the "Agricultural Meteorological Observation Standards for Corn—QX/T361-2016." Soil moisture probes were buried at depths of 10 cm, 20 cm, and 40 cm in each plot to measure soil moisture content at different depths. The irrigation upper and lower limits were determined based on percentages of field capacity (29.5%).

TABLE 1

Classification of Water Control Severity for Summer Corn

| Drought Level | Jointing Stage | Heading Stage | Silking Stage | Maturity Stage |
|---|---|---|---|---|
| Normal | >60% | >70% | >75% | >70% |
| Mild drought | 50%-60% | 60%-70% | 65%-75% | 60%-70% |
| Middle Drought | 40%-50% | 50%-60% | 55%-65% | 50%-60% |
| Severe Drought | 35%-40% | 45%-50% | 50%-55% | 45%-50% |
| Extreme Drought | ≤40% | ≤45% | ≤50% | ≤45% |

Rapid Drought Monitoring and Discrimination Method:

1) Data Acquisition: This includes multispectral imagery data obtained through unmanned aerial vehicle (UAV) multi-payload low-altitude remote sensing technology and ground-measured chlorophyll content data. The multispectral imagery data is used to calculate NDVI, RENDVI, and SAVI vegetation indices. The acquisition of multispectral imagery data involves using an FL-81 quadrotor UAV integrated with a multispectral camera to capture multispectral aerial images. The flight height is set at 55 meters, corresponding to a ground resolution of 4 centimeters. The camera lens can capture wavelengths including blue, green, red, red-edge, and near-infrared bands. For ground-measured chlorophyll content, a chlorophyll content analyzer, SPAD-502Plus, is used to measure SPAD values. Eight plants are selected in each plot to measure the relative chlorophyll content (SPAD) of their leaves, and the average value is taken as the SPAD value for that plot. The formula for calculating the absolute chlorophyll content Cab/µg cm$^{-2}$ of the leaves is as follows:

$$Cab = 0.11 SPAD^{1.5925}.$$

The calculation formulas for the vegetation indices in this implementation are adopted from Table 2.

TABLE 2

Formulas for Calculating Vegetation Indices

| Vegetation Index | Calculation Formula |
|---|---|
| NDVI | NDVI = $(\rho_{NIR} - \rho_R)/(\rho_{NIR} + \rho_R)$ |
| SAVI | SAVI = $1.5(\rho_{NIR} - \rho_R)/(\rho_{NIR} + \rho_R + 0.5)$ |
| RENDVI | RENDVI = $(\rho_{NIR} - \rho_{RE})/(\rho_{NIR} + \rho_{RE})$ |

Note:
$\rho_{NIR}$, $\rho_R$, $\rho_G$, $\rho_B$, and $\rho_{RE}$ represent the reflectance of the near-infrared, red, green, blue, and red-edge bands, respectively.

2) Development of Chlorophyll Content Inversion Models for Different Drought Levels and Growth Stages of Summer Maize: The NDVI-OTSU method is used for soil background removal and extraction of pure vegetation index pixel values for the summer maize canopy. NDVI, RENDVI, and SAVI vegetation indices are selected to construct three types of regression equations with measured chlorophyll content across different growth stages, and the regression equation with the highest correlation with chlorophyll content for each growth stage is selected as the optimal model equation for that stage. The different growth stages refer to the jointing stage, heading stage, silking stage, and maturity stage. The three types of regression equations are linear, exponential, and logarithmic.

Figure 4:
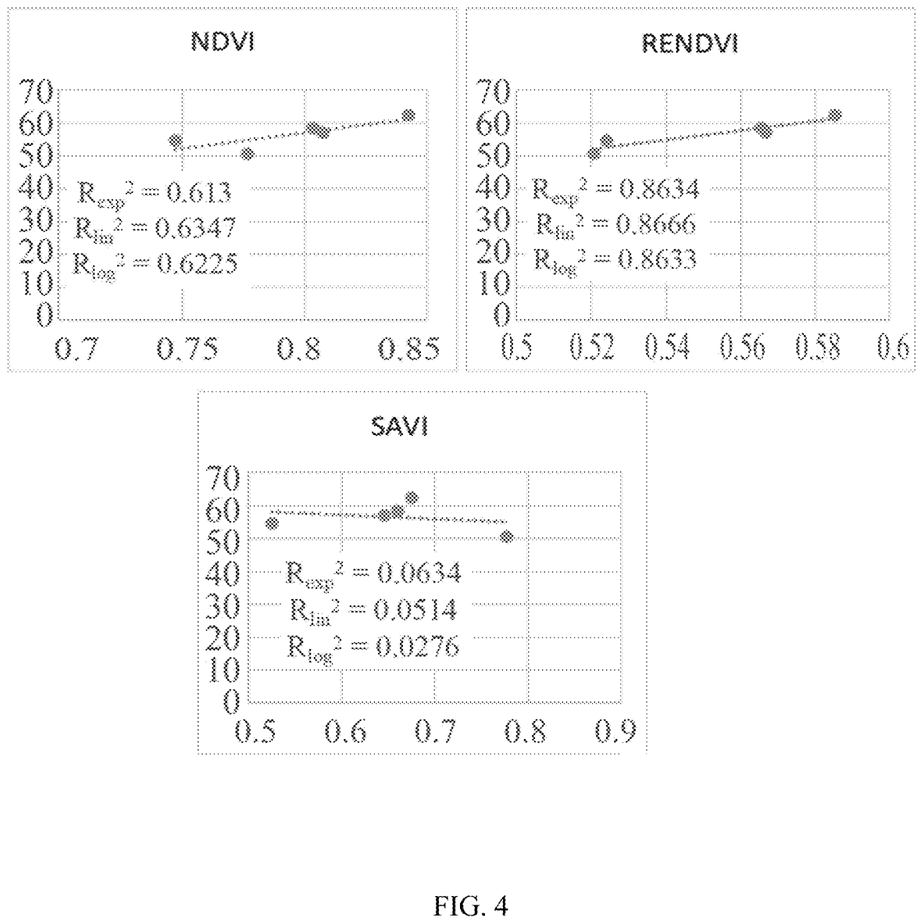
FIG. 4 shows the correlation between various vegetation indices and chlorophyll content for three models during the heading stage in Embodiment 1 of the invention.
Figure 5:
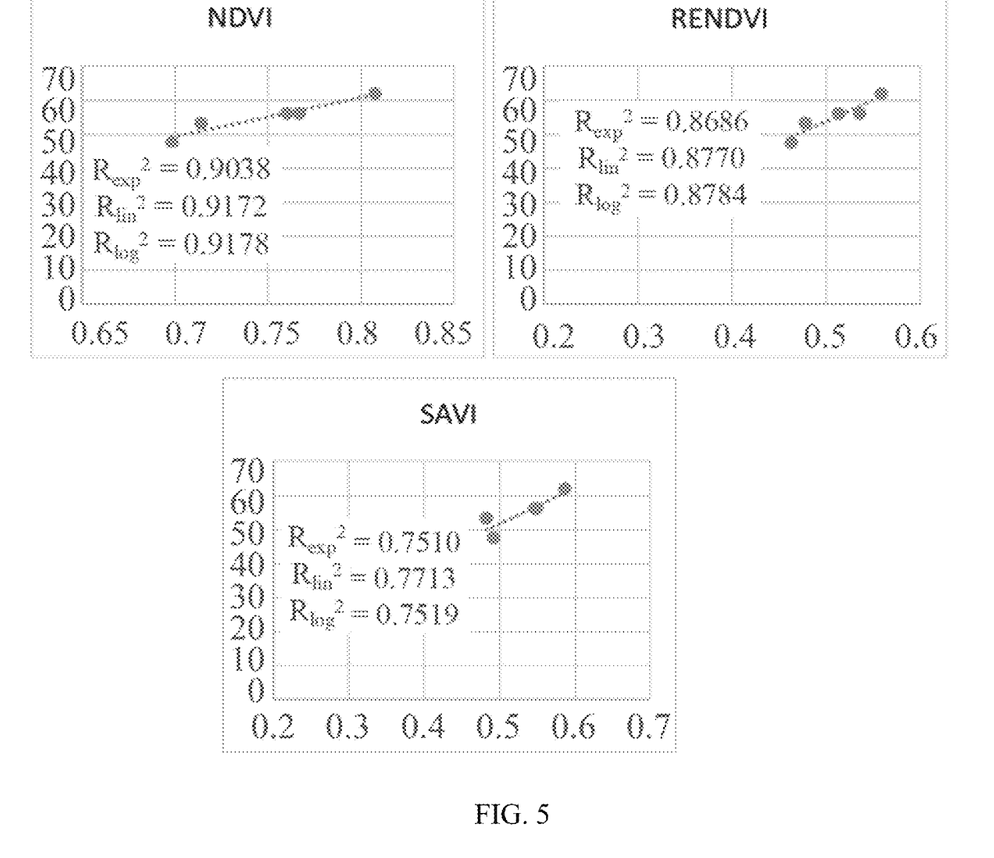
FIG. 5 shows the correlation between various vegetation indices and chlorophyll content for three models during the silking stage in Embodiment 1 of the invention.
Figure 6:
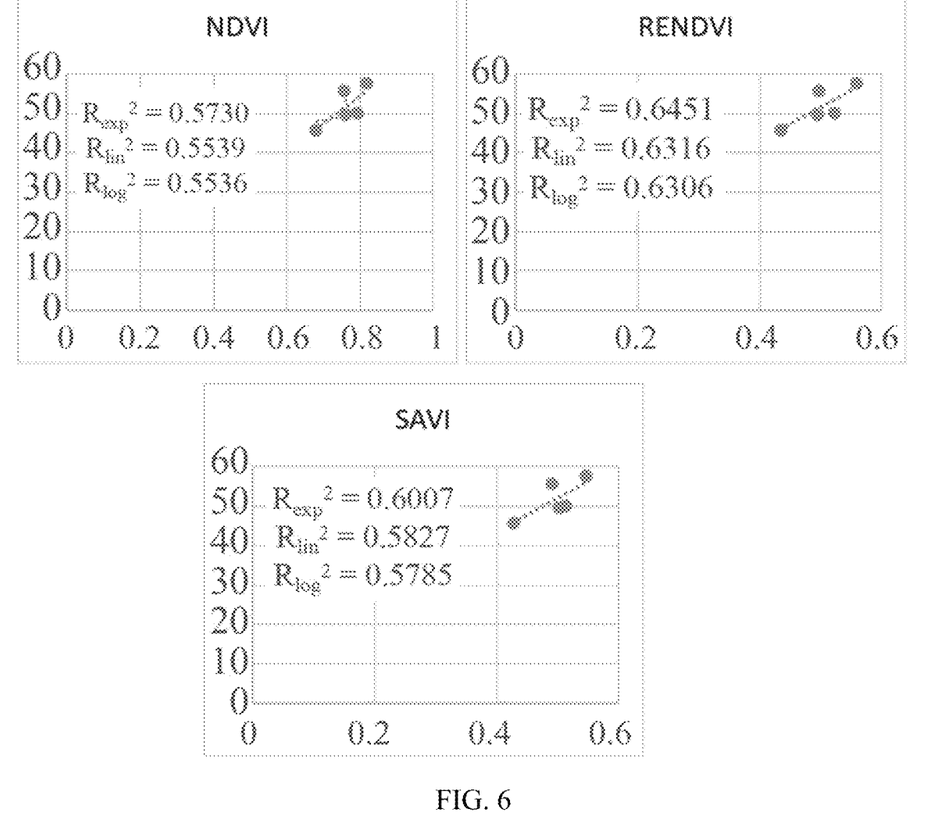
FIG. 6 shows the correlation between various vegetation indices and chlorophyll content for three models during the maturity stage in Embodiment 1 of the invention.
Figure 7:
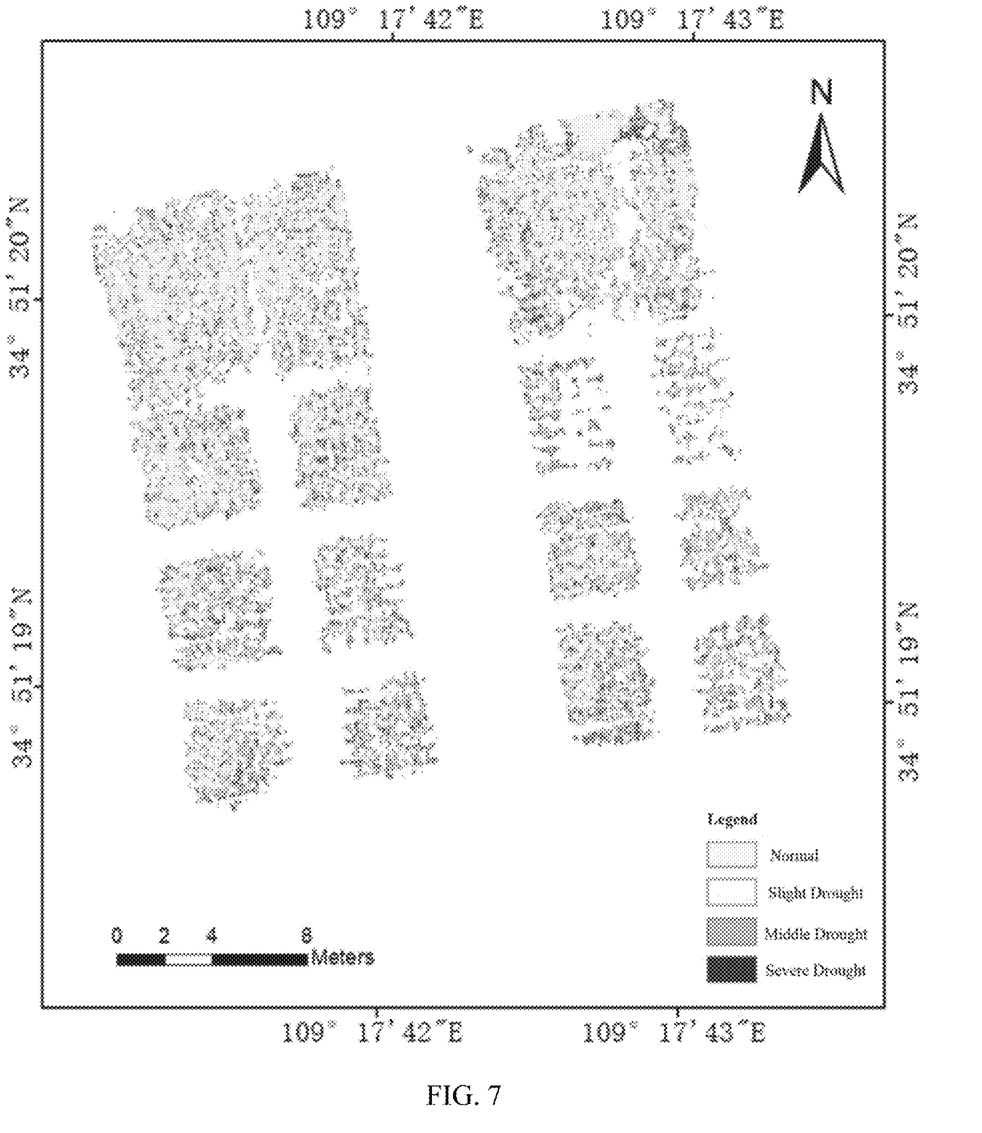
FIG. 7 shows the inversion results of chlorophyll content for the jointing stage.
Figure 8:
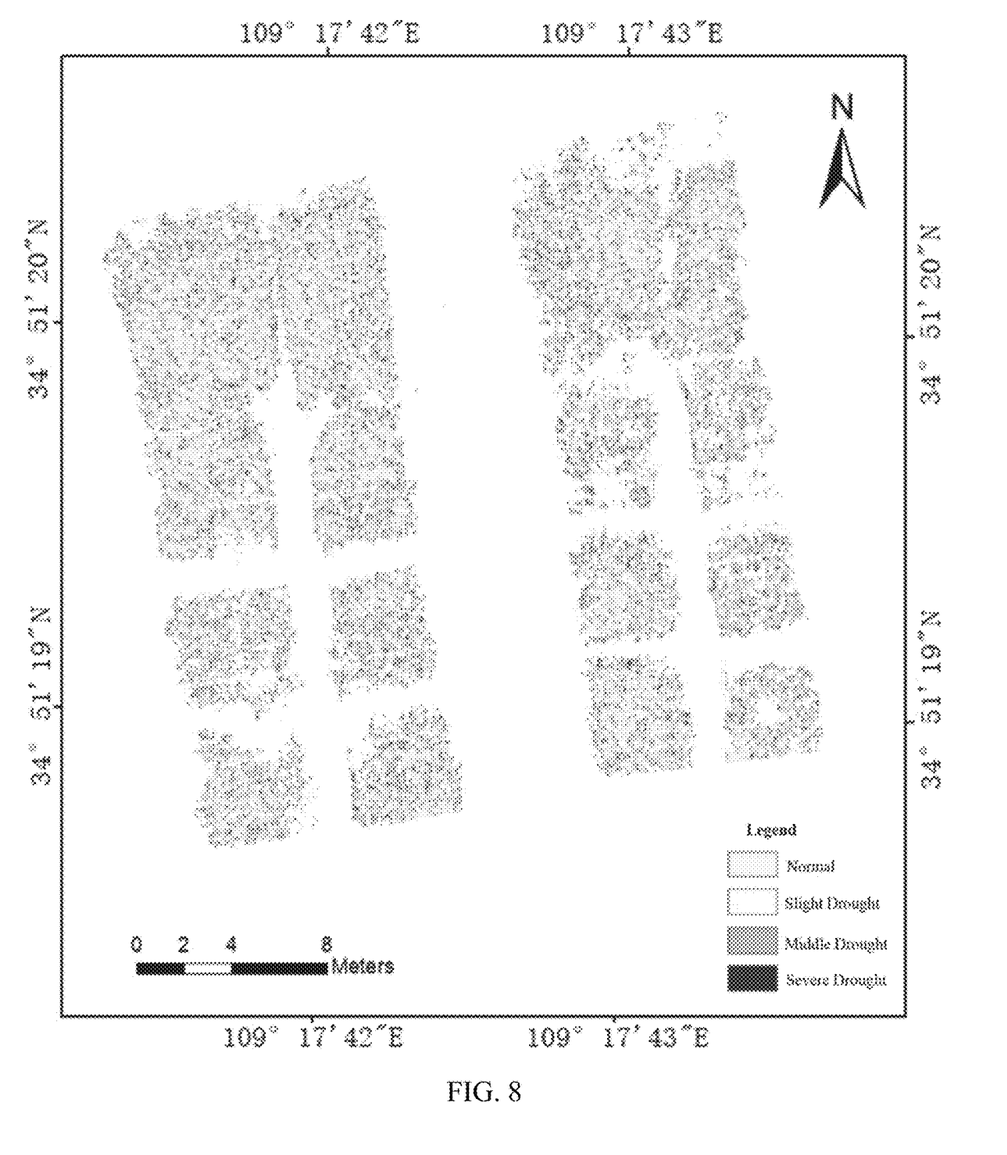
FIG. 8 shows the inversion results of chlorophyll content for the heading stage.
Figure 9:
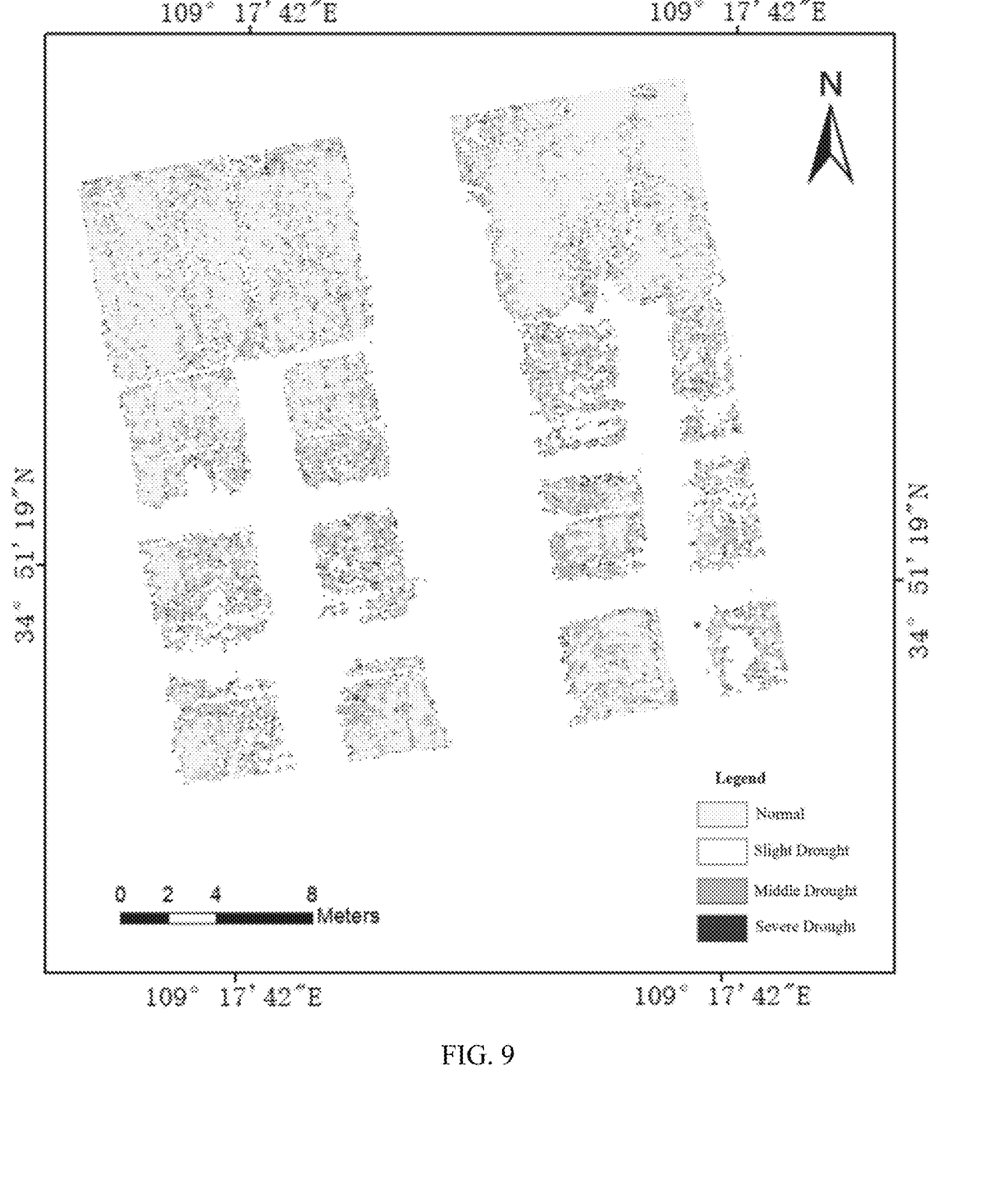
FIG. 9 shows the inversion results of chlorophyll content for the silking stage.
Figure 10:
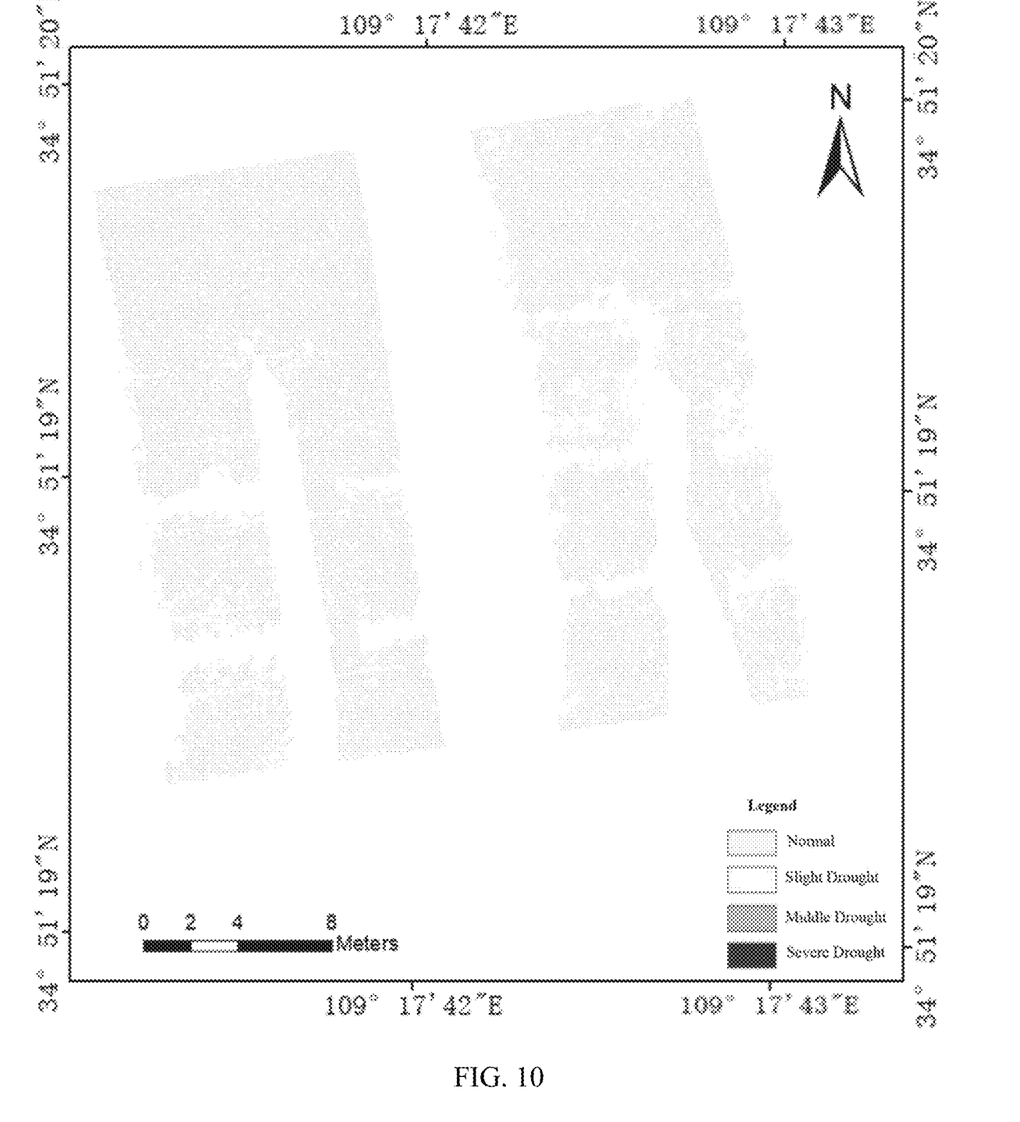
FIG. 10 shows the inversion results of chlorophyll content for the maturity stage.

From the multispectral data, vegetation indices NDVI, EVI, RENDVI are extracted and subjected to regression analysis with measured chlorophyll content to obtain three regression models for vegetation indices and chlorophyll content at different drought levels during each growth stage, as shown in FIGS. 4-6. The overall correlation between SAVI, NDVI, RENDVI vegetation indices, and chlorophyll content inversion is good, with $R^2$ values above 0.55. The correlation is better in the late jointing stage and silking stage than in the heading stage and maturity stage. The logarithmic model between NDVI and chlorophyll content during the silking stage has the highest correlation, with $R^2=0.9178$.

Figure 3:
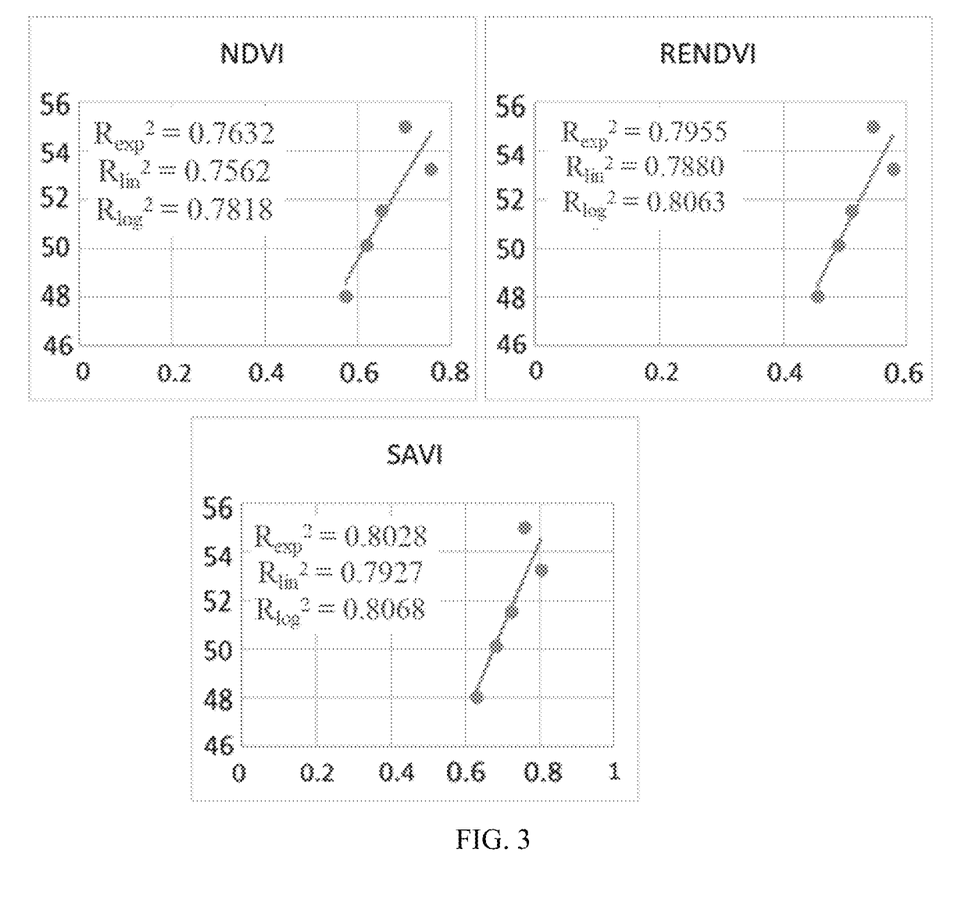
FIG. 3 shows the correlation between various vegetation indices and chlorophyll content for three models during the late jointing stage in Embodiment 1 of the invention.

During the jointing stage, the correlation between the three regression models and chlorophyll content is generally good, with correlation coefficients around 0.8. Among the three models, the logarithmic model has a higher correlation than the exponential and linear models. The exponential and logarithmic models between SAVI and chlorophyll content, and the logarithmic model between RENDVI and chlorophyll content, all have correlation coefficient values above 0.8. The models between NDVI and chlorophyll content all have correlation coefficients greater than 0.7. The best correlation is observed for the logarithmic model between SAVI and chlorophyll content, with $R^2=0.8068$. Therefore, SAVI is selected as the vegetation index to invert chlorophyll content in summer maize during the jointing stage, thereby monitoring the drought severity of different plots during this stage. During the heading stage, SAVI, NDVI, and RENDVI vegetation indices are used to invert chlorophyll content. The correlations of the NDVI and RENDVI models are both above 0.6, indicating good inversion results. The correlation between the SAVI and chlorophyll content model is very low, suggesting that SAVI is not suitable for inverting chlorophyll content during the heading stage. The linear model between RENDVI and chlorophyll content has the highest correlation, with $R^2=0.8666$. Therefore, RENDVI is selected as the vegetation index to invert chlorophyll content in summer maize during the heading stage. During the silking stage, the correlation between the three regression models and chlorophyll content is generally good, with $R^2$ values ranging from 0.7519 to 0.9178. The three models between NDVI and chlorophyll content all have $R^2$ values above 0.9, with the logarithmic model having the best correlation. The correlation coefficients of the three models between RENDVI and chlorophyll content are all above 0.85, with little difference in model correlation.

The model correlation between SAVI and chlorophyll content is lower than the first two models, with $R^2$ values for all three models hovering around 0.75, indicating good inversion performance. When inverting chlorophyll content in summer maize during the silking stage, the logarithmic model with the highest correlation between NDVI and chlorophyll content is selected. The overall inversion performance during the maturity stage is lower than that of other growth stages, with an $R^2$ around 0.6. Among the three models, the exponential model has a higher correlation than the logarithmic and linear models. RENDVI has the highest correlation with the chlorophyll content regression model, followed by SAVI and NDVI with chlorophyll content regression models. Among them, the RENDVI exponential model has the highest correlation with chlorophyll content, with an $R^2$ of 0.6451. Therefore, RENDVI is selected as the vegetation index to invert chlorophyll content in summer maize during the maturity stage, thereby monitoring drought severity across different fields during this stage.

TABLE 3

Optimal Regression Equations for Various Vegetation Indices and Chlorophyll Content at Different Growth Stages

| Stages | Vegetation Index | Model Equation |
| --- | --- | --- |
| Jointing Stage | SAVI | $y = 25.807\ln(x) + 60.121$ |
| Heading Stage | RENDVI | $y = 142.82x - 22.363$ |
| Silking Stage | NDVI | $y = 85.878\ln(x) + 79.95$ |
| Maturity Stage | RENDVI | $y = 22.433e^{1.6613x}$ |

Note:
x represents the vegetation index, and y represents the inverted chlorophyll content.

3) Calibration of Chlorophyll Content Thresholds for Different Drought Levels: Based on the optimal model equations obtained in step 2) for each growth period, chlorophyll content is inverted, and thresholds for chlorophyll content between different drought levels are calibrated. Using multispectral imagery obtained by the Feilong-81 drone, crop chlorophyll content is inverted, and drought severity is classified according to the calibrated thresholds in Table 4.

TABLE 4

Calibrated Chlorophyll Content Thresholds for Different Drought Levels in Summer Maize Based on Drone Data

| | Normal | Mild drought | Middle Drought | Severe Drought |
| --- | --- | --- | --- | --- |
| Jointing Stage | >54.9 | 53.1~54.9 | 51.0~53.1 | <51.0 |
| Heading Stage | >65.4 | 59.2~65.4 | 54.1~59.2 | <54.1 |
| Silking Stage | >60.0 | 56.1~60.0 | 52.0~56.1 | <52.0 |
| Maturity Stage | >55.5 | 47.8~55.5 | 43.5~47.8 | <43.5 |

4) Real-time Discrimination of Drought Levels: Multispectral imagery of the field to be tested is obtained through real-time monitoring, and the required vegetation index is calculated. This vegetation index is then input into the optimal model equation for the corresponding growth period calibrated in step 2) to invert the chlorophyll content. This chlorophyll content is then compared with the thresholds for that period obtained in step 3) to determine the real-time drought level.

Based on multispectral imagery data obtained by drones during various growth stages, chlorophyll content in summer maize is inverted to obtain maps of field distributions for different drought levels. As shown in FIGS. 7 to 10, fields in the west 3 and east 6 areas mainly exhibit mild to moderate drought, while fields in the west 4, east 1, and east 2 areas experience severe drought, consistent with expected experimental results. The SAVI logarithmic model can accurately estimate chlorophyll content in summer maize during the late jointing stage. In the heading stage, the west 2 area exhibits mild drought, the east 3 area shows mild to moderate drought, and the east 4, east 1, and east 2 areas experience severe drought, aligning with experimental design. The RENDVI linear model can accurately estimate chlorophyll content in summer maize during the heading stage. The overall inversion performance during the silking stage is good, with non-designed fields mainly showing no drought, designed field west 2 mainly showing no drought and mild drought, east 3 showing moderate drought, and east 4, east 1, and east 2 experiencing severe drought. Among them, west 3 and west 4 still retain some stress characteristics due to earlier control. The NDVI logarithmic model can accurately estimate chlorophyll content in summer maize during the silking stage. For the maturity stage, the experimental design had west 2 as a mild drought area, west 3 as a moderate drought area, east 1 and east 2 as severe drought areas, and east 3 as both moderate and severe drought areas. However, inversion results show that most fields are experiencing mild drought or no drought due to rainfall at that time. The RENDVI linear model is suitable for estimating chlorophyll content in summer maize during the maturity stage. Vegetation indices NDVI, SAVI, and RENDVI, combined with regression models of measured chlorophyll content, can accurately estimate chlorophyll content across different drought levels during various growth stages.

A total of 1,000 sample points near soil moisture sensors buried in each field were selected for accuracy validation. Using the calibrated thresholds, single-indicator accuracy validation was performed for each growth stage. For the jointing to heading stage, 52 sample points did not meet the threshold range, while 948 sample points did, resulting in an accuracy of 94.8%. For the heading to silking stage, 85 sample points did not meet the threshold range, while 915 sample points did, resulting in an accuracy of 91.5%. For the silking to milk-ripe stage, 83 sample points did not meet the threshold range, while 917 sample points did, resulting in an accuracy of 91.7%.

Finally, it should be noted that the above is intended to illustrate the technical scheme of this invention rather than limit it. Although this invention has been described in detail with reference to preferred embodiments, ordinary technicians in this field should understand that modifications or equivalent substitutions can be made to the technical scheme of this invention without departing from the spirit and scope of the technical scheme.

The invention claimed is:

1. A rapid unmanned aerial vehicle (UAV)-based monitoring and discrimination method for drought conditions in summer maize based on chlorophyll content, characterized by the following steps:
   1) obtaining multispectral imagery data by an FL-81 quadcopter integrated with a multispectral camera and ground-measured chlorophyll content data by a chlorophyll content analyzer, calculating, by a processor, vegetation indices NDVI, RENDVI, and SAVI from the multispectral imagery data, wherein the multispectral camera is configured to capture multispectral aerial images, with a flight height set at 55 meters, corresponding to a ground resolution of 4 centimeters, and the camera is capable of capturing wavelengths in blue, green, red, red-edge, and near-infrared bands;
   2) constructing, by the processor, Inversion Models for Chlorophyll Content at Different Drought Levels and Growth Stages of Summer Maize: Performing soil background pixel removal on the multispectral imagery data to extract pure vegetation index pixel values corresponding to the summer maize canopy; selecting the vegetation indices NDVI, RENDVI, and SAVI calculated in step 1) and constructing three types of regression equations (linear, exponential, and logarithmic) with the ground-measured chlorophyll content data at different growth stages; choosing the regression equation with the highest correlation with chlorophyll content for each growth stage as the optimal model equation for that stage; the different growth stages referred to are the jointing stage, heading stage, silking stage, and maturity stage of maize; specifically, the optimal model equation for the jointing stage is a logarithmic model regression equation between SAVI and chlorophyll content, the optimal model equation for the heading stage is a linear model regression equation between RENDVI and chlorophyll content, the optimal model equation for the silking stage is a logarithmic model regression equation between NDVI and chlorophyll content, and the optimal model equation for the maturity stage is an exponential model regression equation between RENDVI and chlorophyll content;
   3) threshold determination for Chlorophyll Content at Different Drought Levels: Using the optimal model equations obtained in step 2) to invert the chlorophyll content at each growth stage and determine thresholds for chlorophyll content between different drought levels;
   4) real-time Drought Level Discrimination: obtaining multispectral imagery of the test field through real-time monitoring and calculating the required vegetation indices; using the vegetation indices to invert the chlorophyll content at each growth stage by substituting them into the optimal model equations obtained in step 2); comparing the inverted chlorophyll content values with the thresholds determined in step 3) to assess the real-time drought level.

2. The rapid UAV-based monitoring and discrimination method for drought conditions in summer maize based on chlorophyll content according to claim 1, characterized in that: In step 1), ground-measured chlorophyll content is determined using the chlorophyll content analyzer to measure the SPAD value; eight plants in each plot are selected to measure the relative chlorophyll content SPAD value of their leaves, and the average value is taken as the SPAD value for that plot; the formula for calculating the absolute chlorophyll content $Cab/\mu g\cdot cm^{-2}$ of the leaves is as follows:
   $Cab=0.11SPAD^{1.5925}$.

3. The rapid UAV-based monitoring and discrimination method for drought conditions in summer maize based on chlorophyll content according to claim 1, characterized in that: The thresholds for chlorophyll content between different drought levels determined in step 3) are as follows: For the jointing stage, normal conditions >54.9, mild drought 53.1-54.9, moderate drought 51.0-53.1, severe drought <51.0; for the heading stage, normal conditions >65.4, mild drought 59.2-65.4, moderate drought 54.1-59.2, severe drought <54.1; for the silking stage, normal conditions >60.0, mild drought 56.1-60.0, moderate drought 52.0-56.1, severe drought <52.0; for the maturity stage, normal conditions >55.5, mild drought 47.8-55.5, moderate drought 43.5-47.8, severe drought <43.5.

4. A method for determining the chlorophyll content thresholds for different drought levels as recited in claim 1, wherein the method for determining the thresholds for chlorophyll content between different drought levels in step 3) comprises: first, calculating the average chlorophyll content for each drought level obtained through inversion; and then, calculating the median value of the averages for adjacent drought levels, and using this median value as the threshold for the different drought levels.

* * * * *